US006793882B1

(12) United States Patent
Verschuur (10) Patent No.: US 6,793,882 B1
(45) Date of Patent: Sep. 21, 2004

(54) STERILIZATION CONTAINER (75) Inventor: Mark Verschuur, Lilydale (AU)

(73) Assignee: Fairmont Medical Products PTY LTD, Bayswater (AU)

(*) Notice: Subject to any disclaimer, the term of this patent is extended or adjusted under 35 U.S.C. 154(b) by 0 days.

(21) Appl. No.: 10/009,307

(22) PCT Filed: May 12, 2000

(86) PCT No.: PCT/AU00/00459

§ 371 (c)(1),
(2), (4) Date: Apr. 11, 2002

(87) PCT Pub. No.: WO00/69476

PCT Pub. Date: Nov. 23, 2000

(30) Foreign Application Priority Data

May 14, 1999 (AU) .............................. PQ0365

(51) Int. Cl.$^7$ ................................ A61L 2/00
(52) U.S. Cl. .................... 422/6; 206/309; 206/361; 206/439; 422/28; 422/40; 422/294; 422/297; 422/300
(58) Field of Search ............... 422/28, 1, 40, 422/294, 297, 300; 206/209, 361, 439

(56) References Cited

U.S. PATENT DOCUMENTS

| 4,022,324 A | | 5/1977 | Schuster |
| 4,362,241 A | | 12/1982 | Williams |
| 4,730,729 A | | 3/1988 | Monch |
| 4,731,222 A | | 3/1988 | Kralovic et al. |
| 4,773,458 A | | 9/1988 | Touzani |
| 5,222,600 A | | 6/1993 | Stoddard et al. |
| 5,228,460 A | | 7/1993 | Sprinkel et al. |
| 5,437,836 A | * | 8/1995 | Yamada ..................... 422/1 |
| 5,534,221 A | | 7/1996 | Hillebrenner et al. |
| 5,569,161 A | * | 10/1996 | Ebling et al. ............... 600/121 |
| 5,620,656 A | | 4/1997 | Wensky et al. |
| 5,730,530 A | | 3/1998 | Stoddard et al. |
| 5,735,609 A | | 4/1998 | Norton |
| 5,945,076 A | * | 8/1999 | Leonard et al. ............. 422/300 |
| 6,162,395 A | * | 12/2000 | Kowanko ................... 422/33 |

FOREIGN PATENT DOCUMENTS

| AU | 17399/95 | 9/1995 |
| AU | 35254/99 | 11/1999 |
| CA | 2230264 | 10/1999 |
| FR | 2543110 | 9/1984 |
| FR | 2654413 | 5/1991 |
| WO | 94/26633 | 11/1994 |

OTHER PUBLICATIONS

Patent Abstracts of Japan, 08230882A (Kaneishi Suzuyuki) Sep. 10, 1996 Abstract.
Patent Abstracts of Japan, 08091339A (Nara Toshiomi) Apr. 9, 1996 Abstract.

* cited by examiner

Primary Examiner—Krisanne Jastrzab
(74) Attorney, Agent, or Firm—Andrus, Sceales, Starke & Sawall, LLP (57) ABSTRACT A container (30) for use in sterilizing an object has a first end (35) and a second end (38). The container (30) is suitably sized to receive an endoscopic telescope (45) for sterilization. Once the endoscopic telescope (45) has been inserted into the container (30), a lid (46) having a vapour permeable section (47) is fitted to the container. The container and object are then sterilized, for example, by autoclaving. After sterilization, use of the container requires a noon-sterile nurse in an operating theatre to push the ends (35, 38) together. A collapsible or deformable portion (42) collapses and the ends (35, 38) move closer together to thereby force the telescope (45) out of the container (30), where is can be removed by a sterile nurse.

34 Claims, 4 Drawing Sheets

STERILIZATION CONTAINER

CROSS REFERENCE TO RELATED APPLICATION

The present application is the U.S. national stage application of International Application PCT/AU00/00459, filed May 12, 2000, which international application was published on Nov. 23, 2000 as International Publication WO 00/69476 in the English language. The International Application claims priority of Australian Patent Application PQ 0365, filed May 14, 1999.

The present invention relates to a container for use in sterilizing an object and to a method for sterilizing an object. The apparatus and method of the present invention are particularly suitable for use in sterilizing medical and surgical equipment.

Surgical operations must be carried out under strict conditions of sterility to minimize infection risk in the patient. To this end, a sterile field is set up in the operating theatre around the patient. Any theatre staff, such as surgeons or nurses, who have to touch the patient during surgery must rigorously scrub and wear sterile surgical gloves. All instruments and equipment used in the surgery must also be sterile.

Surgical equipment is frequently supplied inside sterile packaging which ensures that the equipment inside the packaging is sterile and remains so whilst the packaging remains unopened. However, storage, handling and distribution of the packaging causes the outer surface of the packaging to become non-sterile. To account for this whilst maintaining the sterile field in the operating theatre, surgical teams include a non-sterile nurse who opens the packaging of pieces of surgical equipment and exposes the sterile equipment to a nurse within the sterile field. The nurse within the sterile field then removes the sterile equipment from the packaging. Provided that the non-sterile nurse does not touch the equipment, sterility of the sterile field is not compromised.

A number of pieces of medical and surgical equipment are re-usable. In order to re-use such equipment, it is necessary to sterilize the equipment before use in the next operation. Sterilization of medical and surgical equipment is commonly carried out in an autoclave in which steam at elevated pressure and a temperature of around 134° C. sterilizes the equipment.

Although autoclaving is an effective sterilizing method, difficulties can arise when it is desired to sterilize delicate medical and surgical equipment. In particular a number of pieces of equipment are typically loaded into the autoclave at a time, which can lead to breakage of delicate equipment. Moreover, it can be difficult to maintain sterility of the equipment when it is removed from the autoclave and stored for use in the next operation.

Other methods of sterilisation that are frequently used include exposing the medical apparatus to a sterilising gas, such as ethylene oxide or STERAD, or soaking in a cold sterilizing liquid.

Endoscopic or laparoscopic surgery, also commonly known as key-hole surgery, is become more wide spread. Endoscopic and laparoscopic techniques are low invasive techniques that can dramatically reduce the duration of stays in hospitals by patients. Endoscopic and laparoscopic techniques require the use of telescopes (hereinafter called "endoscopic telescopes" for convenience) to enable the surgeon to see the site of the surgery on a monitor. Endoscopic telescopes comprise an elongated body in the form of a thin tube having an enlarged housing at one end thereof, which housing contains optical components and allows coupling to a camera or video feed. The other end of the endoscopic telescope is inserted into the patient via an incision made in the patient's skin. The endoscopic telescope projects into the sterile field and hence the endoscopic telescope must be sterilized.

BRIEF DESCRIPTION OF THE INVENTION

It is an object of the present invention to provide a method for and an apparatus for use in sterilizing an object such as a piece of medical or surgical equipment.

In one aspect, the present invention provides a method for sterilizing an object comprising placing the object into a container, the container having an opening through which the object is inserted, the container having at least a portion which is adapted to be collapsed or deformed, closing the opening with a vapour permeable closure and placing the container in a sterilizing environment for sufficient time to sterilize the object.

Preferably, the vapour permeable membrane is a water vapour permeable membrane.

Preferably, the vapour permeable membrane is also permeable to liquid water.

Preferably, the vapour permeable membrane is permeable to other liquids, such as sterilizing liquids.

Preferably the step of placing the container in a sterilizing environment includes the step of placing the container in an autoclave and operating the autoclave for sufficient time to sterilize the object. Although autoclaving is the preferred sterilizing method, other sterilizing methods may be used. Such methods may include placing the container in a sterilizing fluid. In such cases, the closure should also be permeable to the sterilizing fluid.

The step of closing the opening of the container preferably comprises the step of affixing a vapour-permeable closure to a rim of the opening. The closure may be affixed to the rim of the opening by an adhesive. The closure may comprise any suitable vapour permeable material. Preferably, the material is also permeable to other fluids, such as gases. However, it is preferred that the closure material does not allow the passage of bacteria therethrough.

In another embodiment, the step of closing the opening comprises placing a lid or cover on or over the opening, which lid or cover includes at least a portion which is permeable to vapour. The lid or cover is preferably a tamper-evident lid or cover that can only be removed from the container in a tamper-evident manner. Such tamper-evident lids or covers are well known and will not be described further.

The closure material may comprise a microporous membrane. More preferably, the closure material comprises a paper or paper-based material. It will be appreciated that the closure material should be resistant to failure under the sterilizing conditions used. For example, a thermoplastic material that melts at a temperature below the temperature used in an autoclave is unsuitable for use in the present invention if autoclaving is to be used to obtain sterilization. A suitable membrane material could be TYVEK, a proprietary material manufactured by DuPont. This would be suitable for use in the STERAD system. Other materials could also be used.

By placing the object in a container and closing the opening in the container, the object is protected from damage by contact with other objects during sterilization by virtue of the object being protected by the container. The closure confines the object within the container and prevents the entry of bacteria into the container after sterilization is complete. Thus, the container also provides a convenient storage container that can maintain sterility of the object.

In another aspect, the present invention provides a container for use in. sterilizing an object, the container being adapted to receive the object, the container having a first end having an opening to allow positioning of the object in the container, a second end located generally opposite the first end and wherein at least a portion of the container is adapted to be collapsed or deformed whereby the first end and the second end are moved relatively towards each other.

Preferably, at least a portion of the container near the first end is collapsible or deformable whereby collapsing or deforming of the collapsible or deformable portion causes the first end to move relatively closer to the second end.

Preferably, the container includes an elongated portion for receiving an elongate object.

Preferably, the container is relatively enlarged at the open end. This allows easier insertion of the object into the container. It also enables the container to hold objects having a relatively enlarged part, for example, such as an endoscopic telescope. Preferably, the container is adapted to contain a piece of medical or surgical equipment, more preferably an elongated medical apparatus, most preferably an endoscopic telescopic.

Preferably, the opening in the first end of the container is sealable by a vapour-permeable closure. The vapour-permeable closure may be affixed to the rim of the opening in the first end to thereby close the opening. The vapour permeable closure may be removed from the open end by peeling. The vapour permeable closure may comprise a paper or paper-based material or a microporous material.

The vapour permeable membrane is preferably a water vapour permeable membrane. The vapour permeable membrane is preferably permeable to liquid water.

In another embodiment, the open end of the container may be closed after insertion of the object to be sterilized has been inserted therein by placing a lid or cap on the open end, which lid or cap includes a vapour-permeable portion. Preferably, the lid or cap is a screw-on lid or cap that has a threaded portion that co-operates with a complementary threaded portion formed on the container. Alternatively, the lid or cap may be a pop-on type.

The lid or cap is preferably provided with a tamper-proof seal or a tamper evident seal. It is especially preferred that the lid cannot be removed from the container after it has been fitted. If the closure is removed, it should be apparent that it has been removed and that sterility has been compromised. Preferably, removal of the closure damages the closure such that it cannot be re-applied to the container.

The lid or cap may be provided with a vapour-permeable portion by forming the lid or cap with an opening and covering the opening with a vapour-permeable material. The vapour permeable material may comprise a paper or paper-based material or a microporous material. Alternatively, the lid or cap may be manufactured from a vapour-permeable material.

The second end of the container may be formed as a closed end. More preferably, the second end of the container is closed by a vapour permeable means. This allows air to circulate through the container after autoclaving to thereby assist in drying any condensed water inside the container.

The vapour permeable means may be a paper or paper-based closure means or a microporous material. In embodiments where the second end is a closed end and is formed from the material of the container, one or more vapour-permeable windows may be provided in the container. Indeed, one or more vapour-permeable windows may be provided even if the second end has a vapour-permeable closure thereon.

In one embodiment of the present invention, the container comprises a first portion and a second portion joined together. The first portion may include the first end and the second portion may include the second end. The first and second portions are preferably formed from plastics material and may be joined by any suitable method, such as welding. The first portion may contain the deformable or collapsible portion, or the second portion may contain the deformable or collapsible portion. Alternatively, both the first portion and the second portion may contain a collapsible or deformable portion.

The container is most preferably designed for use in the sterilization of endoscopic telescopes. In this embodiment, the container has an elongated part into which the endoscopic telescope is inserted and an enlarged portion depending from the elongated part for holding the enlarged part of the telescope. It is preferred that the elongated part has the deformable or collapsible portion. This may be provided by having corrugations or flutes formed in the outer wall(s) of the elongated part. Other arrangements that lead to a collapsible or deformable portion may also be used.

In a most preferred embodiment of the container embodiment for use in sterilizing endoscopic telescopes, the container comprises a first part and a second, elongated part joined to the first part. The first part is of relatively enlarged diameter (with respect to the elongated part). The first part may include an outwardly projecting part having an open end that fits relatively snugly with the second, elongated part such that the outwardly projecting part of the first part overlaps with a part of the second elongated part. The overlapping parts may be joined together, eg, by welding (or by any other joining technique). In this fashion the overlapping parts may reinforce each other and provide greater strength to the elongated part of the container.

A part of the container may be provided with indicating means to indicate whether or not the container has been exposed to a sterilising environment. The indicating means may be a colour change portion that undergoes a colour change when exposed to the sterilising environment. The colour change may be caused by exposure to elevated temperature or the sterilising gas. Preferably, the indicating means forms part of the vapour permeable closure.

The container of the present invention provides a container for containing a piece of medical or surgical equipment during sterilization. The container protects the medical or surgical equipment from damage during sterilization. By closing the open end of the container with the vapour permeable closure, sterilization of the medical or surgical equipment can be achieved and the medical or surgical equipment can be stored in sterile conditions inside the container following sterilization. The container may include indication means to indicate if the container has been sterilised. The indicator means is preferably a replaceable vapour permeable closure.

Moreover, the provision of a collapsible or deformable portion allows the equipment inside the container to be easily accessed during a surgical operation. In particular, in use in a surgical operation, the non-sterile nurse removes the closure and then collapses or deforms the collapsible or deformable portion of the container. Consequently, the sterile piece of medical or surgical equipment inside the container is at least partially exposed and the sterile nurse can grasp the exposed part and remove the sterile equipment from the container. The container of the present invention allows the sterilized equipment to be removed therefrom without the non-sterile nurse having to touch the sterile inner part of the container and the sterile equipment inside the container. The sterile nurse does not have to touch the non-sterile outer surface of the container.

The collapsible or deformable portion of the container is preferably made to collapse or deform in a concertina fashion. To this end, the collapsible or deformable portion may include a plurality of fold lines or lines of weakness extending around the container. It will be appreciated that the present invention also includes any other collapsible or deformable portion. For example, the container may include a portion made from a pliant material or include a portion able to be folded back upon itself, or include a corrugated or fluted portion.

The collapsible or deformable portion may comprise a portion of the container at or adjacent to the first end of the container which is adapted to fold downwardly upon the container. This action will move the first and second ends relatively closer together.

The container may be made from any material that is resistant to the conditions encountered in sterilization. The container is preferably made from suitable plastics material. Polyetheylene is particularly preferred. The container may be made in one piece or it may be made from two or more pieces joined together. Containers of varying size may be made to accommodate telescopes or other instruments of varying size. The inside surface of the container is preferably hydrophobic or treated to be hydrophobic. The container may also be gamma-ray permeable to leave open the possibility of using in gamma-ray sterilization.

In another aspect, the present invention provides a container for use in sterilizing an object, the container adapted to receive the object, the container having an internal volume for receiving the object, and an opening through which the object can be inserted into the container, characterized in that the container is adapted to be separated into at least two parts to thereby expose the object.

Preferably, the container has a first end and a second end and a portion of the container between the first end and the second end is adapted to be breakable to thereby enable separation of the container into at least two parts. The breakable portion may comprise one or more lines of weakness, or a portion made of a low-breaking point material.

The container is preferably provided with a closure means to close the opening in the container. The closure means is preferably a tamper proof or tamper-evident closure. More preferably, the closure means cannot be removed from the container once it has been fitted thereto. If the closure means is removed, it should be apparent that the closure means has been removed, to thereby indicate that sterility has been compromised.

The container preferably has a vapour permeable portion. The vapour permeable portion may be part of the container, or it may be part or all of the closure.

The vapour permeable portion may be as described with reference to the other aspects of the invention described herein.

The closure means may be as described with reference to the other aspects of the present invention.

In this aspect of the invention, the container with an object inside is sterilized. After sterilization, use of the container in an operating theatre requires the non-sterile nurse to grasp the object in both hands and break the container into the at least two portions. The sterile nurse can then remove the object from the portion that still holds the object.

In all aspects of the present invention, the container may further comprise a sheet-like material adapted to drape over the object upon removal of the object from the container. The sheet-like material may be mounted to the inside of the container. Alternatively, the sheet-like material may be mounted to the closure means. The sheet-like material is preferably a sheet of gauze or other medical fabric. By draping over the object as it is removed from the container, the sheet-like material provides a further barrier between the object and the non-sterile part of the container to further reduce the chance of compromising sterility

BRIEF DESCRIPTION OF THE DRAWING

A preferred embodiment or the present invention will now be described with reference to the accompanying drawings in which:

In FIG. 9, an endoscopic telescope is also shown inside the container.

DETAILED DESCRIPTION OF THE INVENTION

The embodiment of the present invention shown in the attached figures is particularly useful in the sterilization of medical or surgical equipment by autoclaving and for convenience the embodiment of the invention will be described with reference to autoclaving. However, it is to be understood that the present invention is equally applicable to use in other sterilization methods besides autoclaving and that the invention should not be considered to be limited solely to autoclaving. Furthermore, the embodiment shown in the attached figures relate to the sterilization of an endoscopic telescope. Again, it will be appreciated that medical or surgical equipment other than endoscopic telescopes may be sterilized in accordance with the present invention and that it is not intended that the present invention be restricted to the sterilization of endoscopic telescopes.

Figure 1:
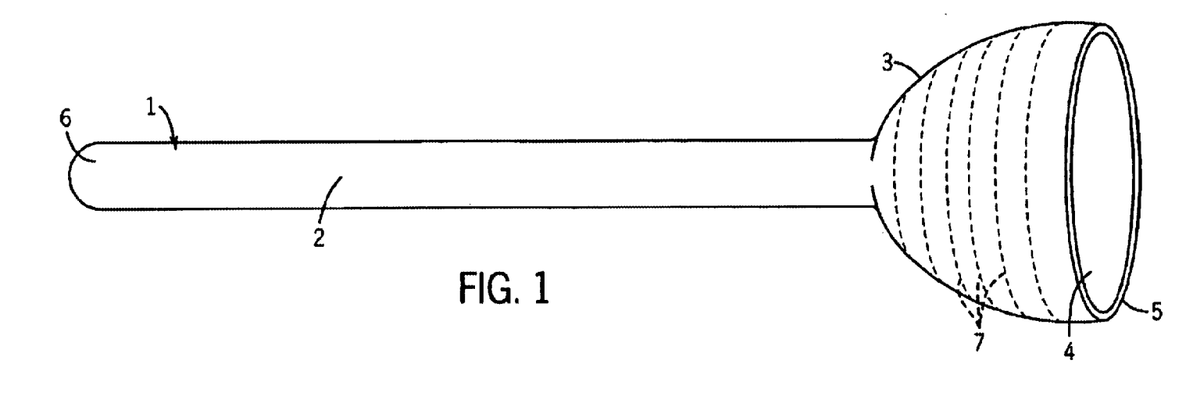
FIG. 1 shows a perspective side view of a container in accordance with the present invention.
Figure 3:
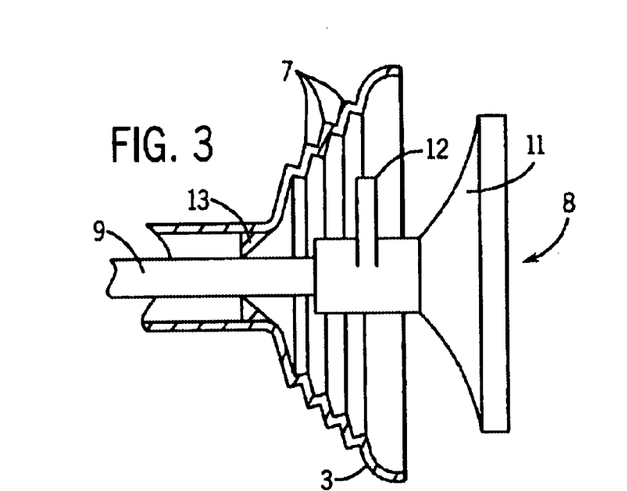
FIG. 3 shows a cross-sectional side view of the apparatus of FIG. 2 but showing how the endoscopic telescope is removed from the container.

Turning now to consider FIG. 1, a container 1 in accordance with the present invention includes an elongate tubular portion 2, and an enlarged portion 3 at the proximal end of the container. The enlarged portion 3 includes an open end 4 defined by a rim 5. The container also includes a second, closed end 6 that is located generally opposite the open end 4. The enlarged portion 3 includes a series of fold lines or lines of weakness 7, indicated in dashed outline. The fold lines or lines of weakness 7 allow the enlarged portion 3 to be collapsed upon itself in concertina like fashion, as best shown in FIG. 3.

Figure 2:
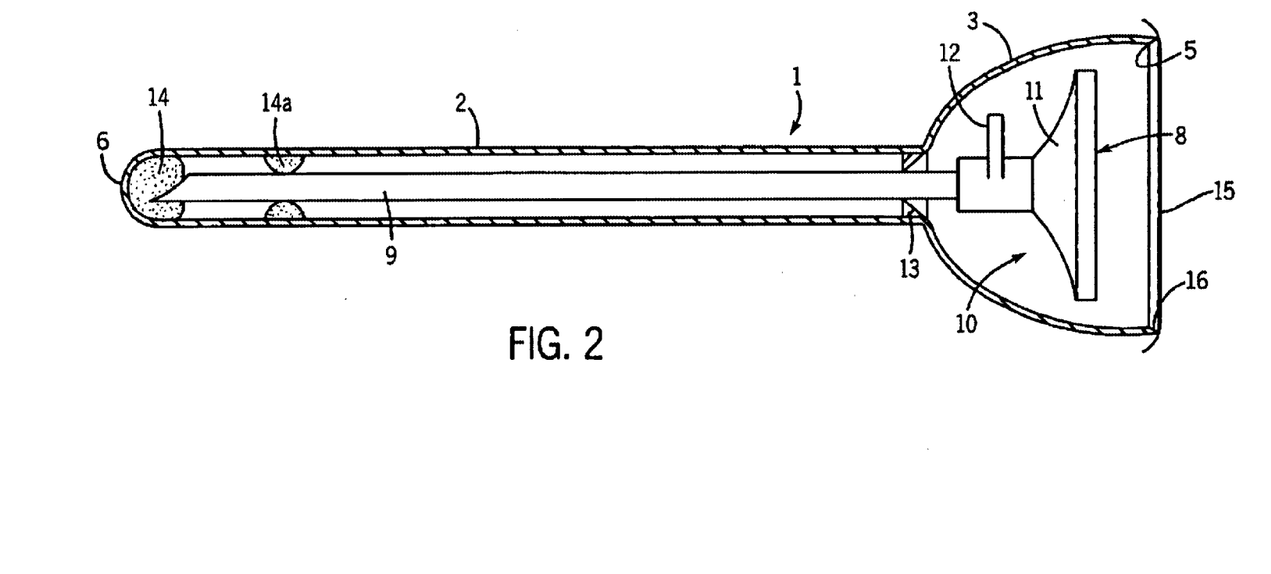
FIG. 2 shows a cross-sectional side view of the container of FIG. 1 with an endoscopic telescope positioned within the container.

Turning now to consider FIG. 2, which shows a cross-sectional view of the container of FIG. 1 as filled with an endoscopic telescope, the container 1 of FIG. 2 is shaped to receive an endoscopic telescope 8. The endoscopic telescope 8 includes an elongate portion 9 that extends into the elongate portion 2 of container 1. The endoscopic telescope 8 also includes a proximal end 10 that includes a housing 11 for housing optical components and a clamping means 12. As can be clearly seen from FIG. 2, the enlarged end 10 of the endoscopic telescope 8 fits inside the enlarged portion 3 of container 1. To assist in inserting the elongate portion 9 of endoscopic telescope 8 into the elongate portion 2 of endoscopic telescope 1, a tapered guide 14a is fitted to the elongate part 2 of the container 1. The elongate part 2 of container 1 is also fitted with sponge holder 13 and sponge padding 14 to provide support for the end of the endoscopic telescope.

After the endoscopic telescope 8 is inserted through the opening 4 in container 1, vapour permeable closure 15 is affixed to the opening to thereby close the opening 4. In the embodiment shown in the figures, the vapour permeable closure 15 comprises a paper or paper base material that is affixed to the container by adhesive 16 that contacts the rim 5 of the opening 4. Although FIG. 2 shows the water vapour permeable closure 15 extending beyond the edges of the container, it will be appreciated that the vapour permeable closure 15 may sit flush with the edges of the container. The vapour permeable closure is preferably water vapour permeable and is also preferably permeable to liquid water.

In order to sterilize the endoscopic telescope, the container 1 having the endoscopic telescope 8 placed therein and vapour permeable closure 15 affixed thereto is placed inside an autoclave. Operation of the autoclave causes steam and possibly water to pass through vapour permeable closure 15 and into the inner volume of container 1. This results in sterilization of the endoscopic telescope. At the end of the autoclave cycle, the autoclave is turned off and is depressurised. Any water that has condensed inside container 1 can run out of the container and permeate through permeable closure 15. This leaves the inside of the container 1 substantially dry. In this regard, it will be noted that although lines of weakness or fold lines 7 are formed in the enlarged portion of the container 1, in the uncollapsed state shown in FIGS. 1 and 2, the inside of the enlarged portion 3 of container 1 presents a substantially smooth surface that does not collect any condensed water.

Once the container shown in FIG. 2 is removed from the autoclave, it may be stored for future use. The inside of the container remains sterile because permeable closure 15 prevents the entry of bacteria into the container. Moreover, the container 1 provides protection for the endoscopic telescope 8 against bumps and rough handling.

When it is time to use the endoscopic telescope 8 in a surgical procedure, the container 1 containing endoscopic telescope 8 is transferred to the operating theatre. In the operating theatre, a non-sterile nurse picks up the container 1 and collapses or deforms the enlarged portion 3 by pulling the enlarged portion 3 towards the closed end 6. It will be appreciated that the permeable closure 15 is either removed prior to deforming the enlarged portion 3 or is removed by the act of deforming the enlarged portion 3. As best shown in FIG. 3, deforming the enlarged portion 3 by urging it towards the second, closed end 6 causes the open end 4 to move relatively towards the second, closed end 6. The enlarged portion 3 collapses or deforms in a concertina like manner around fold lines or lines of weakness 7. This has the effect of exposing enlarged end 10 of endoscopic telescope 8 from the open end 4 of container 1. A sterile nurse can then grasp the end 10 of endoscopic telescope 8 and withdraw the endoscopic telescope 8 from the container 1. As the end 10 of endoscopic telescope 8 is sterile, the sterile nurse does not compromise the sterile field in the operating theatre by this operation.

Once the endoscopic container 8 has been removed from the container 1, the container may either be washed ready for resterilization or simply discarded.

Figure 4:
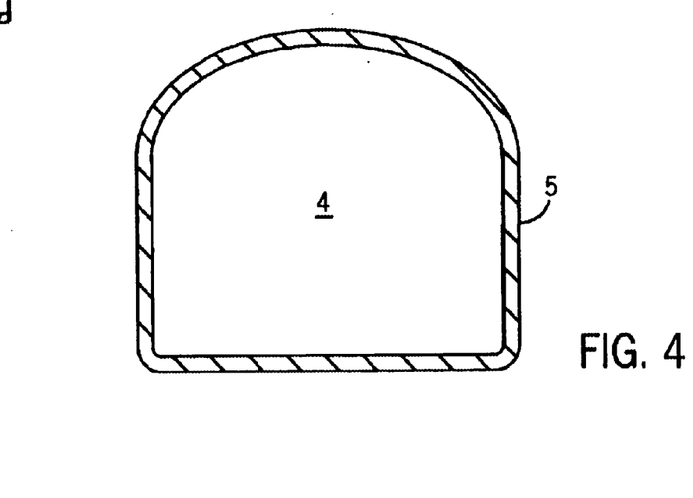
FIG. 4 shows an end view of one embodiment of a container in accordance with the present invention.

The container 1 may have any suitable profile. In one embodiment, best shown in FIG. 4, the enlarged portion 3 of container 1 has a generally square or rectangular profile, with the rim 5 of open end 4 defining that particular profile. The advantage of the profile shown in FIG. 4 is that the container 1 is then stackable on other similar containers for ease of storage. However, it will be appreciated that any other profile for the container may be used.

Figure 5:
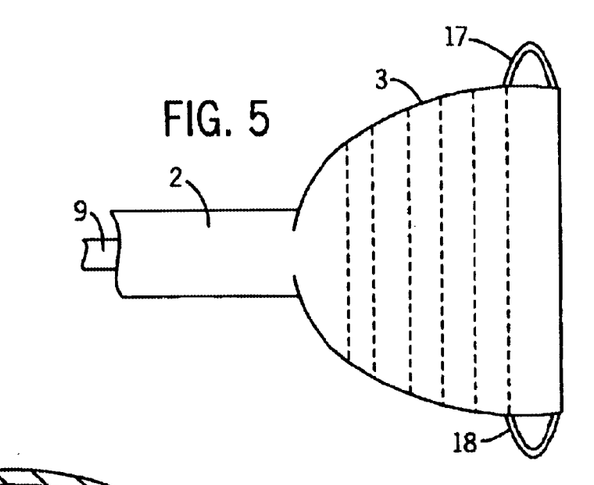
FIG. 5 shows a modification of the container of FIG. 1 having pull rings to simplify collapse of the container.

In order to improve the operation of collapsing the enlarged portion 3 of the container 1, as best shown with reference to FIG. 3, the enlarged portion 3 of container 1 may be provided with ring pulls 17, 18 for grasping by the non-sterile nurse. This is best shown in FIG. 5. Alternatively, pull tabs may be provided.

The container 1 shown in the embodiment of the present invention may be integrally formed as a single unit. Alternatively, the container 1 may be formed from two or more parts that are joined together. For example, the elongate portion 2 of container 1 may comprise an extruded tube. Closed end 6 may be attached to one end of the extruded tube, for example, by ultrasonic welding or by use of a suitable water tight adhesive. Similarly, enlarged portion 3 may be attached to the other end of extruded portion 2, again by ultrasonic welding or by use of a suitable adhesive.

Figure 6:
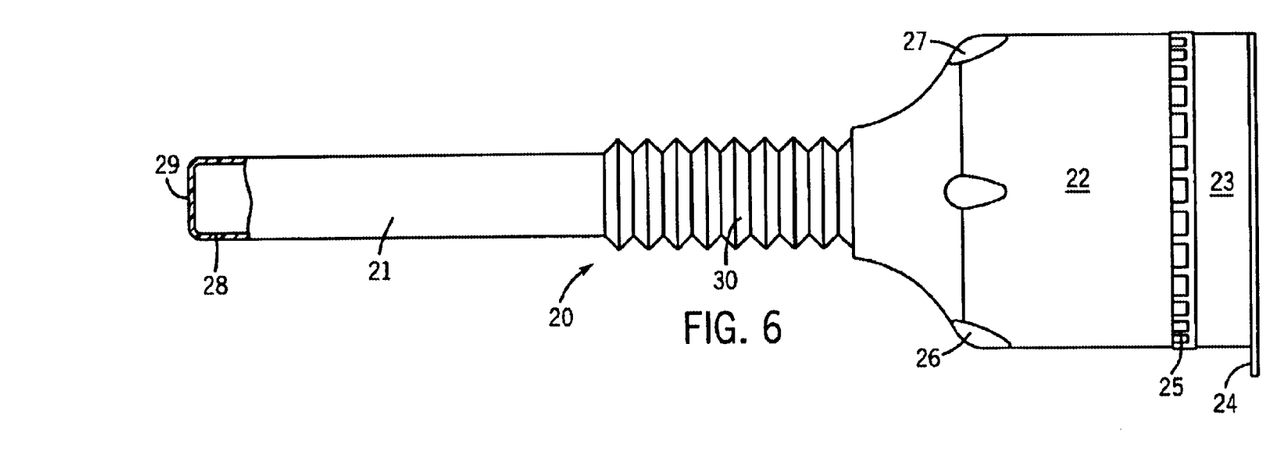
FIG. 6 shows a container in accordance with another embodiment of the present invention.

Turning now to FIG. 6, the container 20 comprises an elongated barrel 21 and an enlarged end portion 22. Enlarged end portion 22 has an open end that is adapted to be closed by screw cap 23. Screw cap 23 has a peel paper seal 24 adhered thereto. The peel paper seal 24 closes an opening in screw cap 23. Although not shown in FIG. 6, screw cap 23 crews on to a threaded portion formed on the end of container 20. The screw cap 23 is also provided with a tamper proof or tamper evident seal 25. This seal may be similar to those found on bottles of fruit juice. The tamper proof or tamper evident seal provides a further level of security to the medical staff that the contents of the container are sterile and have not been opened following sterilisation.

The peel paper seal also may include a colour change portion that changes colour, preferably irreversibly, under sterilising conditions. This portion gives an indication to the medical staff as to whether the contents of the container have been sterilised.

The enlarged end portion 22 also includes finger indentations 26, 27 that are designed to assist in grasping and using the container.

The second end 28 of the container has an opening formed therein and a paper seal 29 is applied over that opening. The paper seal 29 allows air to permeate therethrough and this then permits drying of any water that may have condensed inside the container during sterilization.

The container 20 shown in FIG. 6 is also provided with corrugations 30 that allow the pull back exposure of the telescope. Corrugations 30 are provided in the barrel of the container. In particular, the container can be collapsed by moving the ends of the container towards each other, which thereby causes the corrugations to collapse upon themselves.

The container 20 shown in FIG. 6 is preferably made from polyetheylene, which is a heat resistant plastic. However, any other heat resistant material may be used as the material of construction for the container. The screw cap 23 may be made of nylon or polycarbonate to enhance adhesion of the peel paper seal 24 to the screw cap. The peel paper seal applied to the screw cap may have printing thereon to advise users of the contents of the container and also to include information such as the date the contents were sterilized, the sterilizing conditions and the operator who performed the sterilization procedure.

Figure 7:
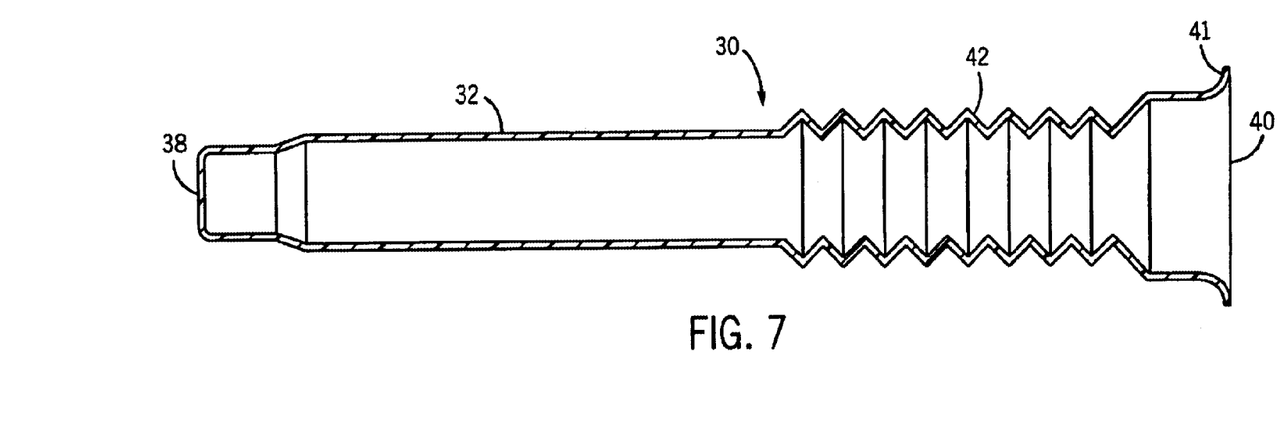
FIG. 7 shows a side view in cross-section of an elongated part of a container in accordance with another embodiment of the present invention.
Figure 8:
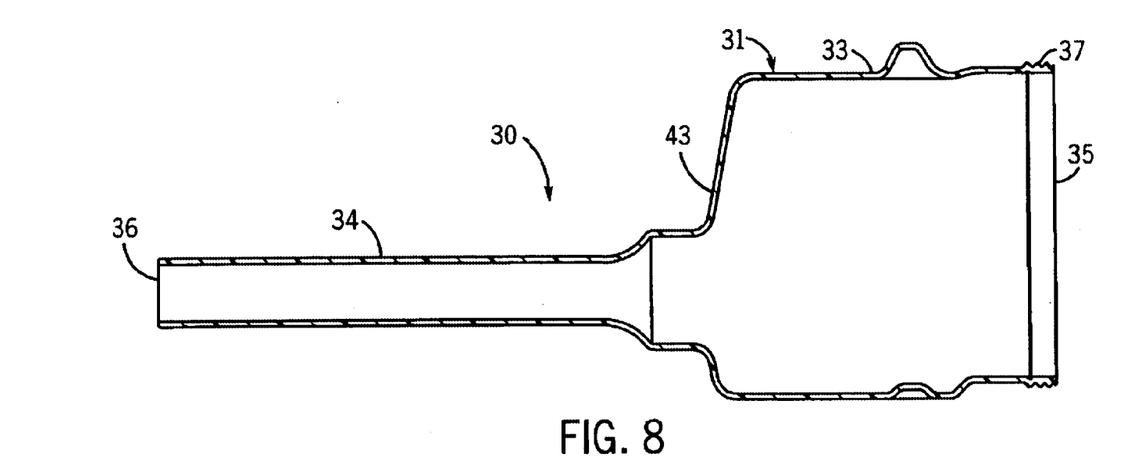
FIG. 8 shows a side view in cross-section of an enlarged part of a container in accordance with another embodiment of the present invention.
Figure 9:
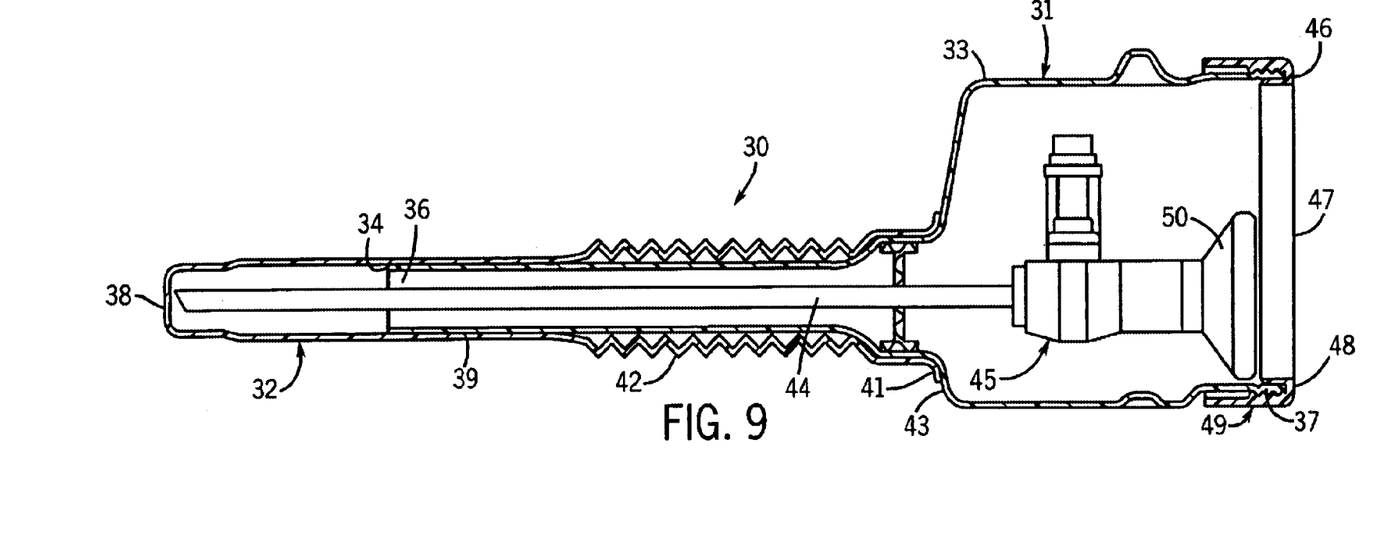
FIG. 9 shows side view in cross-section of the container made from the parts of FIGS. 7 and 8.

Turning now to the embodiment of the present invention shown in FIGS. 7 to 9, the container 30 comprises a first part 31 (best shown in FIG. 8) and a second part 32 (best shown in FIG. 7). The first part 31 includes a portion of enlarged diameter 33 and an outwardly extending projecting part 34 of relatively small diameter. The first part 31 has a large opening 35 through which an endoscopic telescope can be inserted and a small opening 36 in a generally opposed end thereof. The barrel portion of an endoscopic telescope can extend through opening 36.

The first part 31 is preferably made from a plastics material. Suitably, first part 31 is made by blow molding or injection molding.

The elongated portion 34 of the first part 31 may suitably comprise a relatively thin walled section of little strength. This allows the elongated section 34 to be readily deformed in use.

The first part 31 may also be provided with an outwardly extending ridge 37, which ridge facilitates the fitment of a cap or lid over the opening 35.

The second part 32, best shown in FIG. 7, comprises a closed end 38, an elongated hollow portion 39 and an open end 40. Open end 40 has a flange 41 projecting radially outwardly therefrom. The second part 32 includes a corrugated portion 42 which allows the closed end 38 to be displaced relatively towards the open end 40.

In order to produce the final container 30, as shown in FIG. 9, the elongated part 34 of the first part 31 is inserted into the hollow elongated part 39 of the second part 32. The flange 41 of the second part 32 then comes into abutment with wall portion 33. The first part 31 is then joined to the second part 32 by ultrasonically welding the flange 41 to the wall portion 43. Second part 32 is suitably made from a rigid plastics material and second part 32 may be made by blow molding or injection molding. Second part 32 provides a degree of strength and reinforcement to elongated part 34 of first part 31.

In use of the container 30 shown in FIG. 9, an endoscopic telescope 45 having an elongated barrel 44 is inserted through large opening 35. As can be seen from FIG. 9, the length of the container 30 is slightly longer than the length of the endoscopic telescope 45. Once the endoscopic telescope 45 has been inserted into container 30, a lid or cap 46 having a vapour permeable part 47 is affixed to the container 30. Lid or cap 46 is arranged such that it cannot be removed from the container 30 or, if it is removed, it is evident that the container 30 has been tampered with.

Lid 46 suitably comprises an annular part 48 having a flange 49 depending therefrom. Flange 49 has fixing means for fixing the lid to the complementary shaped lugs 37 on container 30. The vapour permeable part 47 of lid 46 suitably comprises a vapour permeable paper that is joined to the annular part 48 of the lid or cap 46. Once the lid 46 has been placed on the container 30, the container 30 is placed into a sterilizing environment, for example into an autoclave or into a gas sterilizer that uses ethylene oxide or a STERAD (a proprietary gas sterilizing system marketed by Johnson & Johnson). The vapour permeates through the vapour permeable portion 47 of lid 46 to thereby sterilize the endoscopic telescope located inside the container 30. Once the sterilizing cycle has been completed, the container 30 is removed from the sterilizing apparatus and placed into storage until the endoscopic telescope 45 is required for use. As can be seen from FIG. 9, the container fully surrounds the sterilized endoscopic telescope and seals the endoscopic telescope 45 from the outside environment. Accordingly, the endoscopic telescope remains in a sterile condition whilst it is in the container 30. When it comes time to use the endoscopic telescope, it is taken to the operating room. There, the non-sterile nurse holds the container 30 in both hands, with one hand being on first part 31 and the other hand being on second part 32. The non-sterile nurse pushes the closed end 38 towards the first part 31. This results in the corrugated portion 42 collapsing upon itself and the closed end 38 moving relatively towards the first part 31. The closed end 38 then comes into contact with the end of the barrel 46 of the endoscopic telescope 45. This pushes the endoscopic telescope 45 to the right (as shown in FIG. 9) and as a result the endoscopic telescope 45 breaks through the vapour permeable section 47 of lid 46. Once the endoscopic telescope 45 has been exposed, a sterile nurse grasps the end 50 of the endoscopic telescope and fully withdraws the endoscopic telescope 45 from the container 30. Container 30 may then be discarded.

The cap 46 may be used to record information for hospital or surgical use, including sterilization information (eg date and conditions), patient information etc.

Where the cap includes the facility for recording patient information, the vapour permeable part 47 of cap 46 may be removed from the container and placed on the patient's chart.

The vapour permeable part 47 is most preferably a peel-paper that is applied to the annular part 46 of the cap 45.

Although the embodiment described with reference to FIGS. 7 to 9 shows the first part 31 and second part 32 connected to each other by welding, it will be apparent that any other joining technique may also be used. For example, an adhesive or adhesive tape may be used.

The first and second parts may suitably be made from polyethylene, polypropylene or other suitable plastics material. The walls of the container 30 may be at least partially translucent or transparent in order to enable visual inspection of the contents of the container. Alternatively, the contents of the container may be written on the peel-paper 47.

In a modified method of using the apparatus shown in FIGS. 7 to 9, the endoscopic telescope 45 may be placed in the first part 31 prior to joining the first part 31 and second part 32 together. The distal end of endoscopic telescope 45 may protrude beyond open end 36 of first part 31. Lid 46 would then be fitted. The second part 32 would be placed over the outwardly projecting part 34 of first part 31 to thereby fully enclose the telescope 45 inside the container 30 and the first and second parts 31, 32 would then be joined together, eg, by welding, by adhesive, by tape, etc.

The container of the present invention may be made in a number of different lengths to suit different types of telescopes for sterilization. It will also be appreciated that although FIGS. 1 to 6 show the invention used in conjunction with the sterilization of endoscopic telescopes, the invention may be extended to cover the sterilization of a number of different types of medical apparatus.

It will be appreciated that the invention described herein is susceptible to variations and modifications other than those specifically described. It is to be understood that the invention encompasses all such variations and modifications that fall within its spirit and scope.

What is claimed is:

1. A container for sterilizing an object, the container adapted to receive the object, the container having a first end having an opening to allow positioning of the object in the container, a second end located generally opposite the first end and closure means for closing the opening in the first end, said closure means comprising a vapor permeable sterility barrier, and wherein at least a portion of the container is collapsible or deformable to relatively move the first end and the second end towards each other to extend the object towards the opening in the first end.

2. A container as claimed in claim 1 wherein the closure means comprises a vapor permeable closure for affixing to a rim of the opening.

3. A container as claimed in claim 2 wherein the vapor permeable sterility barrier comprises a peel paper or a vapor permeable membrane.

4. A container as claimed in claim 1 wherein the closure means comprises a lid or cap having a vapor permeable sterility barrier.

5. A container as claimed in claim 4 wherein the lid or cap comprises an annular member having a flange depending therefrom, said flange having interengaging means for engaging with corresponding interengaging means on the container to thereby hold the lid or cap on the container, and a vapor permeable sterility barrier spanning an opening in the annular member.

6. A container as claimed in claim 4 wherein the lid or cap is a tamper-proof or tamper-evident lid or cap.

7. A container as claimed in claim 1 wherein the collapsible or deformable portion comprises a fluted or corrugated portion.

8. A container as claimed in claim 1 wherein the container is relatively enlarged at the first end.

9. A container as claimed in claim 1 wherein the second end of the container comprises a closed end.

10. A container as claimed in claim 1 wherein the second end is closed by a vapor permeable means.

11. A container as claimed in claim 1 wherein the collapsible or deformable portion is produced from a relatively rigid material.

12. A container as claimed in claim 1 comprising a first portion and a second portion joined together to form the container.

13. A container as claimed in claim 12 wherein the first portion includes the deformable or collapsible portion.

14. A container as claimed in claim 12 wherein the second portion includes the deformable or collapsible portion.

15. A container as claimed in claim 12 wherein the first portion and the second portion each contain a deformable or collapsible portion.

16. A container as claimed in claim 1 for use in sterilizing medical equipment comprising an elongated part for receiving said medical equipment and an enlarged part depending from the elongated part.

17. A container as claimed in claim 16 wherein the elongated part includes the collapsible or deformed portion.

18. A container as claimed in claim 17 comprising a first part and a second, elongated part joined to the first part, the first part being of relatively enlarged diameter with respect to the elongated part.

19. A container as claimed in claim 18 wherein the first part includes an outwardly projecting part that fits relatively snugly with the second, elongated part such that the outwardly projecting part of the first part overlaps with at least some of the second, elongated part.

20. A container as claimed in claim 19 wherein the second part has an open end for receiving the outwardly extending part of the first part and a closed end, said closed end comprising the second end of the container.

21. A container as claimed in claim 20 wherein the first part has an open end in the outwardly extending part through which a barrel of an endoscopic telescope can pass and a large opening in the enlarged diameter portion.

22. A container for sterilizing an object, the container having an internal volume for receiving the object, an opening through which the object can be inserted into the container, and closure means for closing the opening, said closure means comprising a vapor permeable sterility barrier, characterized in that the container has a first end and a second end and a portion between the first and second ends that is breakable to enable separation of the container into at least two parts, thereby to expose the object.

23. A container as claimed in claim 22 wherein the breakable portion comprises one or more lines of weaknesses or a portion made of a low-breaking point material.

24. A container as claimed in claim 22 wherein the closure means is a tamper proof or tamper evident closure.

25. A container as claimed in claim 22 further comprising a sheet-like material adapted to drape over the object upon removal of the object.

26. A container as claimed in claim 25 wherein the sheet-like material is mounted to the inside of the container.

27. A container as claimed in claim 25 wherein the sheet-like material is mounted to a closure means.

28. A container as claimed in claim 25 wherein the sheet-like material is a sheet of gauze or other medical fabric.

29. A container as claimed in claim 1 wherein the deformable or collapsible portion comprises a portion of the container at or adjacent to the first end of the container which is adapted to fold downwardly upon the container.

30. A method for sterilizing an object comprising placing the object into a container, the container having an opening through which the object is inserted, the container having first and second ends and at least a portion which is deformable or collapsible by moving a first end of the container relatively towards a second end of the container, closing the opening with a vapor permeable sterility barrier and placing the container in a sterilizing environment for sufficient time to sterilize the object.

31. A method as claimed in claim 30 wherein the object is removed from the container by removing the vapor permeable sterility barrier and collapsing or deforming the collapsible or deformable portion by relatively moving a first end of the container and a second end of the container toward each other to thereby reduce an inner volume of the container and extend the object at least partly out of the container.

32. A container as claimed in claim 1, wherein said vapor permeable sterility barrier is breakable such that collapsing or deforming said collapsible or deformable portion causes the object to break through said sterility barrier for removal.

33. A container as claimed in claim 16, wherein the medical equipment comprises a barrel of an endoscopic telescope.

34. A method for sterilizing an object comprising placing the object into a container, the container having an opening through which the object is inserted, the container having first and second ends and at least a portion which is deformable or collapsible by relatively moving a first end of the container and a second end of the container toward each other, closing the opening with a vapor permeable sterility barrier and placing the container in a sterilizing environment for sufficient time to sterilize the object, wherein the object is removed from the container by collapsing or deforming the collapsible portion to thereby reduce an inner volume of the container and force the object to break open the vapor permeable sterility barrier and extend at least partly out of the container.

* * * * *